United States Patent [19]

Midha et al.

[11] Patent Number: 5,632,998
[45] Date of Patent: May 27, 1997

[54] PERSONAL CARE COMPOSITIONS CONTAINING HYDROPHOBIC GRAFT COPOLYMER AND HYDROPHOBIC, VOLATILE SOLVENT

[75] Inventors: Sanjeev Midha, Blue Ash; Raymond E. Bolich, Jr., Maineville, both of Ohio

[73] Assignee: The Procter & Gamble Company, Cincinnati, Ohio

[21] Appl. No.: 616,847

[22] Filed: Mar. 15, 1996

[51] Int. Cl.$^6$ .............. A61K 7/075; A61K 7/11; A61K 7/08
[52] U.S. Cl. ............ 424/401; 424/70.1; 424/70.12
[58] Field of Search ................ 424/70.1, 70.12

[56] References Cited

U.S. PATENT DOCUMENTS

| | | | |
|---|---|---|---|
| 3,697,643 | 10/1972 | Shepherd et al. | 424/63 |
| 3,907,984 | 9/1975 | Calvert et al. | 424/47 |
| 4,059,688 | 11/1977 | Rosenberg et al. | 424/71 |
| 4,722,958 | 2/1988 | Sauer et al. | 524/379 |
| 4,798,721 | 1/1989 | Yahagi et al. | 424/70 |
| 4,963,348 | 10/1990 | Bolich, Jr. et al. | 424/71 |
| 4,981,902 | 1/1991 | Mitra et al. | 524/547 |
| 4,981,903 | 1/1991 | Garbe et al. | 524/547 |
| 4,985,239 | 1/1991 | Yahagi et al. | 424/70 |
| 4,988,506 | 1/1991 | Mitra et al. | 424/81 |
| 5,009,880 | 4/1991 | Grollier et al. | 424/47 |
| 5,019,377 | 5/1991 | Torgerson | 424/70 |
| 5,021,477 | 6/1991 | Garbe et al. | 424/70 |
| 5,073,371 | 12/1991 | Turner et al. | 424/401 |
| 5,073,372 | 12/1991 | Turner et al. | 424/401 |
| 5,104,642 | 4/1992 | Wells et al. | 424/47 |
| 5,120,531 | 6/1992 | Wells et al. | 424/70 |
| 5,120,532 | 6/1992 | Wells et al. | 424/70 |
| 5,166,276 | 11/1992 | Hayama et al. | 525/329 |
| 5,219,560 | 6/1993 | Suzuki et al. | 424/63 |
| 5,223,179 | 6/1993 | Connor et al. | 252/548 |
| 5,256,407 | 10/1993 | Gough | 424/71 |
| 5,286,755 | 2/1994 | Kauffmann et al. | 514/944 |
| 5,290,555 | 3/1994 | Guthauser et al. | 424/401 |
| 5,324,507 | 6/1994 | Dubief et al. | 424/70 |
| 5,338,541 | 8/1994 | Matz et al. | 424/71 |
| 5,356,627 | 10/1994 | De Cunha et al. | 424/401 |
| 5,362,485 | 11/1994 | Hayama et al. | 424/70 |
| 5,372,804 | 12/1994 | Khoshdel et al. | 424/59 |
| 5,374,421 | 12/1994 | Tashiro et al. | 424/70.12 |
| 5,391,368 | 2/1995 | Gerstein | 424/70.13 |
| 5,540,853 | 7/1996 | Trinh et al. | 510/101 |
| 5,556,616 | 9/1996 | Janchitraponvej et al. | 424/70.122 |

FOREIGN PATENT DOCUMENTS

| | | | |
|---|---|---|---|
| 647849 | 6/1992 | Australia | A61K 00/07 |
| 0412704A2 | 2/1991 | European Pat. Off. | A61K 7/06 |
| 4314305A1 | 3/1994 | Germany | A61K 7/11 |
| 2-25411 | 1/1990 | Japan . | |
| WO92/21319 | 12/1992 | WIPO | A61K 7/06 |
| WO95/04518 | 2/1995 | WIPO | A61K 7/06 |
| WO95/05800 | 3/1995 | WIPO | A61K 7/48 |

Primary Examiner—Thurman K. Page
Assistant Examiner—Sharon Howard
Attorney, Agent, or Firm—Loretta J. Henderson; John M. Howell; David L. Suter

[57] ABSTRACT

The present invention relates to personal care compositions, especially hair care compositions, containing non-silicone, hydrophobic graft copolymers and a hydrophobic, volatile solvent for the copolymer, the solvent being selected from branched chain hydrocarbons, silicones and combinations thereof. This invention also relates to hair conditioners and hair styling products such as rinses, leave on conditioners, and combination shampoo products useful for cleansing, styling and conditioning the hair.

The graft polymers should satisfy the following three criteria:

(1) the graft portion is covalently bonded to the polymeric backbone portion;

(2) the molecular weight of the graft portion is at least about 500; and (3) when used in a composition, such as a personal care composition for application to the hair or skin, the polymeric backbone portion should permit the graft polymer to deposit on the intended surface, such as hair or skin.

Preferred copolymers, when dried, phase-separate into a microphase which includes the graft portion and a microphase which includes the polymeric backbone portion.

22 Claims, No Drawings

PERSONAL CARE COMPOSITIONS CONTAINING HYDROPHOBIC GRAFT COPOLYMER AND HYDROPHOBIC, VOLATILE SOLVENT

TECHNICAL FIELD

The present invention relates to personal care compositions, especially hair care compositions, containing a hydrophobic graft copolymer and a hydrophobic, volatile solvent for the copolymer. Examples of hair care compositions to which this invention relates are hair conditioners and hair styling agents including rinses, leave on conditioners, and combination shampoo products useful for cleansing, styling and conditioning the hair.

BACKGROUND OF THE INVENTION

The use of polymeric materials in hair care products is of increasing importance. In the hair care area, polymers can be used for hair hold and setting products, for hair conditioning products, and in shampoos. For example, rinse-off hair care conditioning/styling products typically comprise a hydrophobic polymer which remains after rinsing the hair. The polymer is solubilized in a suitable solvent which evaporates to leave the polymer treated hair. The solvent must be one in which the polymer is substantially soluble (i.e., the solvent is generally hydrophobic).

A hair styling polymer should provide certain styling benefits. For example, the styling polymer should not leave the hair feeling and looking coated. Also, the styling polymer should have sufficient adhesion without being unduly brittle such that the hair can be restyled, e.g. with heated implements, and then maintain the new style. Still in addition, the styling polymer should be deliverable from a shampoo matrix, i.e., it should deposit on the hair during the washing process and remain behind on the hair fibers. Therefore, in the hair styling area, it is desirable to provide polymers which provide improved styling benefits and which can be delivered from a wide variety of matrices, including rinses, leave-on compositions, and shampoos. It is also desirable to provide hair styling compositions which have improved hair feel performance (after application and drying of such compositions) at a particular level of hair conditioning or conversely, improved hair conditioning for a particular level of hair feel performance.

It is well known that polymers can be modified by the incorporation or grafting of silicone. Such polymers have been used heretofore in hair care compositions. See, e.g., U.S. Pat. No. 5,106,609, to R. E. Bolich Jr., et al. issued Apr. 21, 1992; U.S. Pat. No. 4,693,935, to Mazurek, issued Sep. 15, 1987; PCT U.S. application Ser. No. 94/08031, published Feb. 16, 1995, and PCT U.S. application Ser. No. 94/09503, published Mar. 2, 1995. Silicone grafted polymers tend to have a low surface energy and provide unique aesthetic and formulation advantages not usually obtained from non-silicone grafted polymers. Nonetheless, for improved hair adhesion/hold, conditioning, industrial hygiene, formulation opportunities, and/or economics, it is desirable to have alternative, non-silicone polymer based compositions which meet or approach the hair feel properties provided by silicone polymer based materials.

Non-silicone, hydrophobic graft copolymers are well known in the art, but have not been used for personal care applications, such as hair care products. See, e.g., Chemistry and Industry of Macromonomers, Yuya Yamashita (ED.), Huthig & Wepf, New York, 1993; and Macromolecular Design Concept and Practice, Munmaya K. Mishra (Ed.), Polymer Frontiers International, Inc. New York, 1994. Despite the advantages that non-polar graft copolymers can provide, these materials are generally difficult to formulate in solvents used in the personal care industry. It has been found, however, in the present invention that the use of certain hydrophobic, volatile solvents provides a highly desirable basis for these compositions. The resulting compositions have good styling and conditioning performance and have a highly desirable feel upon the hair, i.e. they do not leave the hair feeling unacceptably stiff or sticky.

The graft copolymers of the present invention are non-silicone, hydrophobic materials, being relatively insoluble in water and/or alcohol and having certain thermomechanical properties. These characteristics make these copolymers highly useful for formulation in hair care products.

It is an object of the present invention to provide novel hair care compositions containing non-silicone, nonpolar graft copolymers.

It is another object of the present invention to provide novel hair care compositions having improved style and hold benefits.

It is another object of the present invention to provide novel hair care compositions having improved conditioning benefits.

These and other objects will become readily apparent from the detailed description which follows.

SUMMARY OF THE INVENTION

The present invention relates to personal care compositions, preferably hair care compositions, comprising:

(A) a graft copolymer having a polymeric backbone and a hydrophobic polymeric side chain grafted to the backbone, said copolymer formed from the copolymerization of randomly repeating A monomer units and B macromonomer units wherein said copolymer comprises:
   (i) from about 30% to about 95% by weight of said A monomer units, wherein said A monomer units are monomer units copolymerizable with said B macromonomer units; and
   (ii) from about 5% to about 70% by weight of said B macromonomer units, wherein said B macromonomer units are hydrophobic macromonomer units having a polymeric portion and a moiety copolymerizable with said A monomer units;

wherein said A monomer units, in conjunction with said copolymerizable moieties of said B macromonomer units, form said polymeric backbone; wherein said polymeric portion of said B macromonomer units forms said hydrophobic polymeric side chain(s); wherein said copolymer has a weight average molecular weight greater than about 10,000; and (B) a hydrophobic, volatile solvent for said copolymer suitable for application to the hair, the solvent being selected from branched hydrocarbons, silicones and combinations thereof.

The copolymer may exhibit at least two distinct $T_g$ values, the first $T_g$ corresponding to said backbone and having a value of at least about 25° C., preferably at least about 30° C.; the second $T_g$ corresponding to the hydrophobic polymeric side chain(s) and having a value of less than about 10° C., preferably less than about 0° C.

The present invention also relates to personal care compositions, preferably hair care compositions, comprising:

(A) a graft copolymer having a polymeric backbone and grafted to the said backbone, the copolymer formed from the copolymerization of randomly repeating A monomer units and B macromonomer units wherein said A monomer units are at least one monomer unit copolymerizable with said B macromonomer units and selected from the group consisting of acrylic acid esters; methacrylic acid esters; N-alkyl acrylamides; vinyl compounds, vinylidene compounds; unsaturated hydrocarbons (e.g., olefins, including straight chain, branched chain, and cycloaliphatic olefins and aromatic ethylenically unsaturated compounds); $C_1$–$C_{18}$ alcohol esters of organic acids and organic acid anhydrides; and combinations thereof; B is a macromonomer unit copolymerizable with said A monomer unit, and corresponding to the formula (I) or (II):

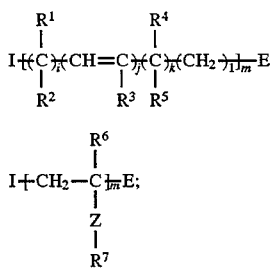

wherein:

"a" is an integer of about 50 or greater, and "b" is, on average, an integer of about 1 or greater;

$R^1$, $R^2$, $R^3$, $R^4$ and $R^5$ are, independently, H or $C_1$ to $C_5$ straight or branched alkyl group;

$R^6$=H or $C_1$ to $C_8$ alkyl;

$R^7$=$C_4$ to $C_{18}$;

Z=

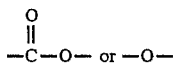

i and k are, independently, an integer of about 1 or greater;

j and l are, independently, an integer of about 0 or greater;

m is an integer from 10 about 2000, preferably from about 15 to 300, and more preferably from about 20 to about 250; and E and I are as defined herein, I preferably selected from the group consisting of hydrogen, C1–40 straight or branched chain alkyl, benzyl, 1-phenyl substituted C2–40 straight or branched chain alkyl, 1,1-diphenyl substituted C2–40 straight or branched chain alkyl, and mixtures thereof and E preferably an ethylenically unsaturated moiety, copolymerizable with the A monomer unit, selected from the group consisting of acrylamide, methacrylamide, vinyl, allyl, acryloyl, methacryloyl, ethacryloyl, 2-vinylbenzoyl, 3-vinylbenzoyl, 4-vinylbenzoyl; 2-vinylbenzyl, 3-vinylbenzyl, 4-vinylbenzyl-1-butenyl, 1-propenyl, isobutenyl, isoprenyl, cyclohexenyl, cyclopentenyl, and mixtures thereof; and (B) a hydrophobic, volatile, solvent for the copolymer which is suitable for application to the hair, the solvent being selected from branched hydrocarbons, silicones and combinations thereof.

The B macromonomer unit can be a homopolymeric macromonomer, or a copolymeric macromonomer containing two or more different randomly repeating monomer units.

In further embodiments, the present invention relates to methods for styling, holding, and/or conditioning hair comprising application of the compositions of the present invention to the hair.

All percentages and ratios used herein are by weight of the total composition and all measurements made are at 25° C., unless otherwise designated. The invention hereof can comprise, consist of, or consist essentially of, the essential as well as optional ingredients and components described herein. All documents referred to herein, including all patents, patent applications, and printed publications, are hereby incorporated by reference in their entirety in this disclosure.

DETAILED DESCRIPTION OF THE INVENTION

"Graft copolymers" is a term familiar to those of ordinary skill in polymer science and is used herein to describe copolymers which result by adding or "grafting" a polymeric chemical moiety (i.e., "grafts") onto another polymeric moiety commonly referred to as the "backbone". The backbone typically has a higher molecular weight than the grafts. Thus, graft copolymers can be described as polymers having pendant polymeric side chains, and as being formed from the "grafting" or incorporation of polymeric side chains onto or into a polymer. The polymer to which the grafts are incorporated can be homopolymers or copolymers, e.g., linear random or block copolymers. Such copolymers are derived from a variety of monomer units.

Thus, the graft copolymers of the present invention can be prepared from the copolymerization of monomer units and macromonomer units such that the macromonomer units are "grafted" or incorporated into the polymer formed from the monomer units. The term "macromonomer" is one familiar to those of ordinary skill in polymer science, and is used to describe a polymeric material containing a polymerizable moiety. In other words, a macromonomer is a macromolecular monomer, which is essentially a high molecular weight type of monomer building block unit which can be used in a polymerization reaction to form polymers with itself, with other monomers, or with other macromonomers.

The term "hydrophobic" is used herein consistent with its standard meaning of lacking affinity for water; whereas "hydrophilic" is used herein consistent with its standard meaning of having affinity for water. As used herein in relation to monomer units, polymeric materials (including the macromonomers and graft copolymer), and solvent for the graft copolymer, "hydrophobic" means substantially water insoluble; "hydrophilic" means substantially water soluble. In this regard, "substantially water insoluble" shall refer to a material that is not soluble in distilled (or equivalent) water, at 25° C., at a concentration of 0.2% by weight, and preferably not soluble at 0.1% by weight (calculated on a water plus material weight basis). Such water insoluble materials are typically nonpolar. Similarly in this regard, "substantially water soluble" shall refer to a material that is soluble in distilled (or equivalent) water, at 25° C., at a concentration of 0.2% by weight, and are preferably soluble at 1.0% by weight. The weight average molecular weight for purposes of determining substantial water solubility or insolubility of a polymeric material shall be about 10,000, although solubility at higher molecular weight shall also be indicative of solubility at about 10,000. "Soluble", "solubility" and the like for purposes hereof corresponds to the maximum concentration of monomer or polymer, as applicable, that can dissolve in water or other solvent to form a solution that is substantially clear to the naked eye, as is well understood to those skilled in the art. The aforementioned definitions shall also apply to other materials so described herein, to the extent any other definitions regarding such materials are consistent with those stated above.

Graft Copolymers

The hair care compositions of the present invention comprise a graft copolymer. In general the hair care compositions comprise from about 0.1% to about 25%, preferably from about 0.5% to about 20%, and more preferably from about 0.5% to about 10%, and most preferably from about 1% to about 5% of the graft copolymer, by weight of the total composition, although higher or lover amounts can be used depending upon the application.

The graft copolymers of the present invention are characterized by having a relatively high strength, high Tg polymeric backbone with a low Tg, hydrophobic polymeric side chain covalently bonded to and pendant from the polymeric backbone (the hydrophobic side chain is grafted to the polymeric backbone). This combination of polymeric moieties in a single copolymer provides the unique and useful properties of these materials. As will be clear to one skilled in the art and especially from the synthetic examples, the graft copolymer may have one or more hydrophobic side chains grafted to the backbone. In addition, the compositions of the present invention may include, in addition to the graft copolymer, corresponding copolymers having no hydrophobic side chains grafted to the backbone. (As known in the art, synthetic graft copolymerization processes may produce a mixture of polymer molecules containing no, one, or more than one hydrophobic side chain covalently bonded to and pendant from the polymeric backbone. From knowledge of the amount and number average molecular weight of hydrophobic side chains in a polymer sample, and the number average molecular weight of the polymer sample, it is possible to calculate the average number of hydrophobic side chains per polymer backbone.)

$T_g$ is a well known term of art in polymer science used to describe the temperature at which a polymer or portion thereof undergoes a transition from a solid or brittle material to a liquid or rubber-like material. Glass transition temperatures can be measured using standard techniques that are well known to the polymer scientist of ordinary skill in the art. One particularly useful technique for determining glass transitions is differential scanning calorimetry (also known as DSC). The glass transition phenomenon in polymers is described in *Introduction to Polymer Science and Technology: An SPE Textbook*, (eds. H. S. Kaufman and J. J. Falcetta), (John Wiley & Sons: 1977).

The $T_g$ of the backbone of the copolymers herein (i.e. that part of the copolymer not containing the hydrophobic side chains) should be at least about 25° C. Preferably this $T_g$ is greater than about 30° C., more preferably from about 30° C. to about 200° C., even more preferably from about 30° C. to about 175° C., and most preferably from about 35° C. to about 150° C. The $T_g$ of the hydrophobic side chains should be less than about 10° C., preferably from about 0° C. to about –130° C., more preferably from about –20° C. to about –125° C., and most preferably from about –45° C. to about –120° C. The aforementioned $T_g$s of the backbone polymer and of the hydrophobic side chains can be determined on a thin film of the polymer formed solely from the A monomer units or a thin film of the B macromonomer unit prior to copolymerization with the A monomer units.

The copolymers of the present invention may exhibit at least two distinct, immiscible, interspersed microphases. Without being limited by theory, it is believed that the hydrophobic side chains of the copolymers are closely associated with each other and thereby exist substantially in one microphase, while the backbone of the copolymer remains substantially in a separate microphase. It is believed that this phase separation property provides a specific orientation of the graft polymer which results in a desirable combination of tactile feel and film-forming or adhesive benefits.

Microphase separation properties of the graft copolymer can be determined by the following method. The polymer is cast as a solid film out of a solvent (i.e., a solvent which dissolves both the backbone and the graft portions). This film is then sectioned and examined by transmission electron microscopy. Microphase separation is demonstrated by the observation of inclusions in the continuous phase. These inclusions should have the proper size to match the size of the graft macromonomer chain (typically a few hundred nm or less) and the proper density to match the amount of macromonomer present. This behavior is well documented in the literature for polymers with this structure (see, for example, S. D. Smith, Ph.D. Thesis, University of Virginia, 1987, and references cited therein, said thesis and references incorporated by reference herein).

A consequence of this phase immiscibility is that the graft copolymer may exhibit at least two distinct glass transition temperatures or, "$T_g$'s", namely one $T_g$ for the backbone and one $T_g$ for the hydrophobic side chain(s) formed by the B macromonomers.

In addition, when the graft copolymer exhibits at least two such $T_g$'s and the ratio of the backbone to the grafts is from about 50–80% backbone, 20–50 wt % grafts, the hydrophobic grafts tend to microphase separate to form rubbery domains within the backbone matrix. Without intending to be limited by theory, it is believed that these rubbery domains act as energy dissipating sites and decrease the brittleness of the polymer film. Such graft copolymers tend to have both a relatively high polymer extension/flexibility at break and an acceptable tensile strength. Such energy dissipation and its effects on polymer physical properties is described in Mechanical Properties of Polymers and Composites, Second Edition, L. E. Nielsen and R. F. Landel; Marcel Dekker, Inc., New York 1994.

The copolymers of the present invention have a weight average molecular weight (in grams/mole) of at least about 10,000. There is no upper limit for molecular weight except that which limits applicability of the invention for practical reasons, such as viscosity, processing, aesthetic characteristics, formulation compatibility, etc. The weight average molecular weight is generally less than about 5,000,000, more generally less than about 2,500,000, and typically less than about 1,500,000. Preferably, the weight average molecular weight is from about 10,000 to about 5,000,000, more preferably from about 75,000 to about 2,000,000, even more preferably from about 100,000 to about 1,000,000, and most preferably from about 125,000 to about 1,000,000.

The copolymers of the present invention are formed from the copolymerization of randomly repeating A monomer and B macromonomer units, preferably wherein the A monomer units are selected from at least one polymerizable, ethylenically unsaturated monomer unit; and the B macromonomer units are selected from at least one hydrophobic macromonomer unit which contains a polymeric portion and a moiety copolymerizable with the A monomer units, preferably an ethylenically unsaturated moiety which is copolymerizable with the A monomer units. In preferred embodiments of these copolymers, the backbone is formed from the polymerization of the A monomer units with the ethylenically unsaturated portion of the hydrophobic B macromonomer unit. The polymeric portion of the B macromonomer units forms the hydrophobic side chains of the copolymer. The A monomer units and B macromonomer units can be selected from a wide variety of structures as long as the copolymer has the required properties of solubility, $T_g$'s, and molecular weights described herein.

The A monomer units and the hydrophobic B macromonomer units comprise or are derived from hydrophobic monomers and optionally a limited amount of hydrophilic monomers. The particular relative amounts of hydrophilic and hydrophobic monomers can vary as long as the graft copolymer as a whole is soluble in the hydrophobic, volatile, solvent hereof. Solubility of the graft copolymer material (or component thereof) in the hydrophobic, volatile solvents hereof is determined according to whether such material can stay in solution or precipitates out of solution at 25° C. at the concentration present in a given composition. Graft copolymers that are soluble in such solvents typically comprise from about from about 50% to about 100% by weight, of hydrophobic monomers and from about 0% to about 50%, by weight, of hydrophilic monomer units.

By appropriate selection and combination of the particular A monomer units and B macromonomer units, and by the choice of specific relative ratios of the units well within the ability of one of ordinary skill in the art, the copolymers can be optimized for various physical properties such as solubility, $T_g$'s, and the like, and for compatibility with other ingredients commonly used in hair care applications.

A Monomer Units

The A monomer unit is selected from copolymerizable monomers, preferably ethylenically unsaturated monomers. Either a single type of A monomer or combinations of two or more A monomers can be utilized. The A monomers are selected to meet the requirements of the copolymer. By "copolymerizable", as used herein, is meant a material can be reacted with another material (e.g., the A monomer and B macromonomer) in a polymerization reaction using one or more conventional synthetic techniques, such as ionic, emulsion, dispersion, Ziegler-Natta, free radical, group transfer or step growth polymerization. In the present invention, monomers and macromonomers that are copolymerizable using conventional free radical initiated techniques are preferred. The term "ethylenically unsaturated" is used herein to mean a material (including preferred A monomers and B macromonomers) that contains at least one polymerizable carbon-carbon double bond (which can be mono-, di-, tri-, or tetra-substituted). The A monomer units and B Macromonomers preferably consist of monomers that, when polymerized, form a saturated polymer. The A monomer units of the copolymers of the present invention can comprise from about 30% to about 95%, more preferably from about 35% to about 85%, and most preferably from about 50% to about 80%, by weight, of the copolymers.

A wide variety of A monomer units can be used in the present invention, including mixtures of two of more monomers, so long as the $T_g$, molecular weight, and solubility requirements of the graft copolymers are met. The A monomer units include hydrophobic monomer units and optionally hydrophilic monomer units. The polymeric backbone will preferably comprise from about 50% to about 100%, more preferably from about 60% to about 98%, most preferably from about 75% to about 95%, by weight of the polymer, of hydrophobic monomer units, and from about 0% to about 50%, preferably from about 2% to about 40%, more preferably from about 5% to about 25%, of hydrophilic monomer units.

Nonlimiting classes of A monomers useful herein include hydrophobic monomers selected from the group consisting of acrylic acid esters; methacrylic acid esters; N-alkyl acrylamides; vinyl compounds, vinylidene compounds; unsaturated hydrocarbons (e.g., olefins, including straight chain, branched chain, and cycloaliphatic olefins and aromatic ethylenically unsaturated compounds); $C_1$–$C_{18}$ alcohol esters of organic acids and organic acid anhydrides; and combinations thereof.

Representative examples of such hydrophobic monomers include acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl- 1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1–18 carbon atoms with the number of carbon atoms preferably being from about 1–12; dicyclopentenyl acrylate; 4-biphenyl acrylate; pentachlorophenyl acrylate; 3,5-dimethyladamantyl acrylate; 3,5-dimethyladamentyl methacrylate; 4-methoxycarbonylphenyl methacrylate; trimethylsilyl methacrylate; styrene; alkyl substituted styrenes including alpha-methylstyrene and t-butylstyrene; vinyl esters, including vinyl acetate, vinyl neononanoate, vinyl pivalate and vinyl propionate; vinyl chloride; vinylidene chloride; vinyl toluene; alkyl vinyl ethers, including isobutyl vinyl ether and s-butyl vinyl ether; butadiene; cyclohexadiene; bicycloheptadiene; 2,3-dicarboxylmethyl-1,6-hexadiene; ethylene; propylene; indene; norbornylene; β-pinene; α-pinene; and combinations thereof.

Preferred hydrophobic monomers suitable for use as the A monomer units include n-butyl methacrylate, isobutyl methacrylate, t-butyl acrylate, t-butyl methacrylate, 2-ethylhexyl methacrylate, methyl methacrylate, indene, norbornylene, β-pinene, α-pinene, vinyl pivalate, vinyl neononanoate, dicyclopentenyl acrylate, 4-biphenyl acrylate, pentachlorophenyl acrylate, 3,5-dimethyladamantyl acrylate, 3,5-dimethyladamentyl methacrylate, 4-methoxycarbonyphenyl methacrylate, trimethylsilyl methacrylate, t-butyl styrene and combinations thereof. Most preferably, the hydrophobic monomer is selected from t-butyl styrene, t-butyl acrylate, t-butyl methacrylate, and combinations thereof.

Nonlimiting classes of A monomers useful herein also include hydrophilic monomers selected from the group consisting of unsaturated mono-, di- and poly- carboxylic acids; (meth)acrylamides; (meth)acrylates; (meth)acrylate alcohols; organic acid anhydrides; esters of organic acid anhydrides; hydrophilic vinyl compounds; hydrophilic allyl compounds; hydrophilic imides; salts of any such compounds; and combinations thereof.

Representative examples of such hydrophilic monomers include acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), vinyl caprolactam, salts of any acids and amines listed above, and combinations thereof.

Preferred hydrophilic monomers include acrylic acid, N,N-dimethyl acrylamide, dimethylaminoethyl methacrylate, quaternized dimethylaminoethyl methacrylate, vinyl pyrrolidone, salts of acids and amines listed above, and combinations thereof. The quaternized monomers can be quaternized either before or after the copolymerization with other monomers of the graft copolymer.

As used herein, A monomers are meant to include monomers that are unsubstituted or substituted with one or more substituent groups. Exemplary substituent groups include, but are not limited to, alkyl, aryl, carboxyl, halo groups, and combinations thereof.

Hydrophobic B Macromonomer Units

The hydrophobic B macromonomer units of the present invention are large polymeric building blocks containing repeating structural units. The B macromonomers can be formed from the polymerization of smaller monomer units. The B macromonomers encompass a wide variety of structures and are copolymerizable with the A monomer units. Without intending to be limited by theory, the hydrophobic B macromonomer units are believed to contribute to the overall solubility properties of the copolymers.

Either a single type of B macromonomer or combinations of two or more B macromonomers can be utilized, so long as the $T_g$, solubility, and molecular weight requirements of the copolymer are met. Also, each B macromonomer can be constructed from two or more randomly repeating monomer units, in which case the macromonomer would actually be considered a copolymer type of macromonomer. In any event, the B macromonomers are selected to meet the requirements of the graft copolymers. The hydrophobic macromonomers contain hydrophobic monomer units and optionally hydrophilic monomer units.

The hydrophobic B macromonomers comprise from about 5% to about 70%, more preferably from about 15% to about 65%, and most preferably from about 20% to about 50%, by weight of the copolymer.

B macromonomers that are useful herein contain a polymeric portion and a copolymerizable moiety, preferably an ethylenically unsaturated moiety that is copolymerizable with the A units. Typically, the preferred B macromonomers are those that are endcapped with the ethylenically unsaturated moiety. By "endcapped" as used herein is meant that the ethylenically unsaturated moiety is at or near a terminal position of the macromonomer. However, this definition of "endcapped" is not intended to limit the macromonomer to only those macromonomers which terminate in a carbon-carbon double bond (whether mono-, di-, tri-, or tetra-substituted).

The hydrophobic B macromonomers of the present invention can be synthesized utilizing a variety of standard synthetic procedures familiar to the polymer chemist of ordinary skill in the art. Furthermore, these macromonomers can be synthesized starting from commercially available polymers. Typically the weight average molecular weight of the macromonomer is at least about 500, preferably from about 1000 to about 200,000, more preferably from 1500 to about 30,000, and most preferably from about 2000 to about 25,000.

For example, the hydrophobic B macromonomers can be synthesized by the polymerization (acid, base, free radical, or auto-initiated) of one or more hydrophobic monomers, and optionally hydrophilic monomers, to form a polymer which is subsequently reacted with or "endcapped" with a copolymerizable structural unit E, preferably an ethylenically unsaturated moiety. Alternatively, the B macromonomers can be synthesized starting with commercially available hydrophobic polymers which are "endcapped" with the structural unit referred to herein as E. In yet another alternative, the B macromonomer can be synthesized by starting with the structural unit E, and polymerizing onto it the desired hydrophobic monomer units. It is to be understood that in this third alternative, the ethylenically unsaturated moiety of the E unit is not consumed in the synthesis but its integrity is preserved for subsequent copolymerization of the B macromonomer with the A units. All of the synthetic alternatives are merely illustrative in that any other suitable synthetic procedures can be utilized to prepare the B macromonomers and copolymers of the present invention.

The B macromonomer is at least one hydrophobic macromonomer unit copolymerizable with A, corresponding to the formula (I) or (II):

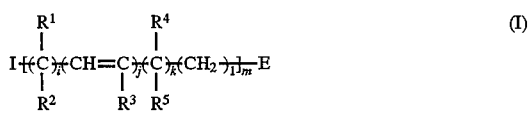

wherein:

$R^1$, $R^2$, $R^3$, $R^4$ and $R^5$ are, independently, H or $C_1$ to $C_5$ straight or branched alkyl group;

$R^6$=H or $C_1$ to $C_8$ alkyl;

$R^7$=$C_4$ to $C_{18}$;

Z=

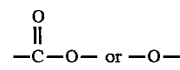

i and k are, independently, an integer of about 1 or greater;

j and l are, independently, an integer of about 0 or greater;

m is an integer from 10 about 2000, preferably from about 15 to 300, and more preferably from about 20 to about 250; and E and I are as defined herein.

E is an ethylenically unsaturated "endcapping" group that is copolymerizable with the A monomer units. Preferably E is selected from the group consisting of acrylamide, methacrylamide, vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, isoprenyl, cyclohexenyl, cyclopentenyl, and combinations thereof. Even more preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and combinations thereof. Most preferred is when E is selected from the group consisting of vinyl, allyl, acryloyl, methacryloyl, ethacryloyl, 3-vinylbenzyl, 4-vinylbenzyl, and combinations thereof.

I is a chemical initiator moiety. Without being limited by theory, I can be derived from a chemical initiator or solvent used in the synthesis of the B macromonomer. Nonlimiting examples of such initiators from which I can be derived include hydrogen ion, hydrogen radical, hydride ion, hydroxide ion, hydroxyl radical, peroxide radical, peroxide anion, C1–20 carbocations, C1–20 carbanions (e.g., sec-butyl carbanions, and 1,1-diphenyl-4-methylpentyl carbanion), C1–20 carbon radicals, C1–20 aliphatic and aromatic alkoxy anions, ammonium ion, substituted ammonium ions (e.g., C1–20 alkyl and C1–20 alkoxy substituted), and C1–20 carbanions (e.g., cumyl carbocation). I can be derived from any useful solvent, nonlimiting examples of which inlcude water, methanol ethanol, propanol, isopropanol, acetone, hexane, dichloromethane, chloroform, benzene, and toluene. Nonlimiting examples of I include chemical moieties selected from the group consisting of hydrogen, C1–40 straight or branched chain alkyl, benzyl, 1-phenyl substituted C2–40 straight or branched chain alkyl, 1,1-diphenyl substituted C2–40 straight or branched chain alkyl, and combinations thereof. More preferably I is selected from the group consisting of 1, 1-diphenyl14-methylpentyl, sec-butyl, and cumyl. Most preferably I is sec-butyl or cumyl.

$R^1$, $R^2$, $R^3$, $R^4$ and $R^5$ are suitably independently derived from monomer units such as those described in reference to the A monomer units. Preferred monomers are selected from the group consisting of ethylenically unsaturated, straight or branched hydrocarbons and ethylenically unsaturated esters of acrylic acid and methacrylic acid. Preferred such monomers are hydrocarbons selected from isobutylene, butadiene, isoprene, 1-butene, 5-methyl-1-hexene, 6-methyl-1-heptene, 4,4-dimethyl-1-pentene etc.; esters of acrylic acid and an alcohol selectcd from n-butyl, dodecyl, 2-ethylhexyl, 2-ethylbutyl, n-ethyl, n-heptyl, n-hexyl, iso-butyl, iso-decyl, iso-propyl, 3-methylbutyl, 2-methylpentyl, nonyl, octyl, and propyl alcohol; and esters of methacrylic acid and an alcohol selected from dodecyl, 2-ethylhexyl, hexyl, decyl, octadecyl, octyl, n-pentyl, and tridecyl alcohol.

Nonlimiting examples of these endcapped hydrophobic macromonomers include acryloyl, methacryloyl, or 2-,3- or 4-vinyl benzyl endcapped polymers of methacrylic or acrylic acid esters, such as, poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate), poly(iso-propyl acrylate), poly(3-methylbutyl acrylate), poly(2-methylpentyl acrylate), poly(nonyl acrylate), poly(octyl acrylate), poly (2-ethylhexyl methacrylate), poly(tridecyl methacrylate), poly(n-pentyl methacrylate), poly(octyl methacrylate), poly(octadecyl methacrylate), poly(dodecyl methacrylate), poly(n-pentyl methacrylate). Other examples include, methacryloyl, acryloyl or 2-, 3-, or 4-vinyl benzyl endcapped polymers of poly(isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly (4,4-dimethyl-1-pentene), and poly(iso-butyl vinyl ether).

Examples of other macromonomers include "copolymer" type B macromonomers containing two or more randomly repeating monomer units. Nonlimiting examples of these "copolymer" type of macromonomers include acryloyl endcapped poly[4-t-butyl vinyl benzene-co-2-ethylhexyl acrylate], poly[2-ethylhexyl acrylate-co-octyl acrylamide), poly[2-ethyl vinyl benzene-co-octyl methacrylate)], and the like.

The endcapped hydrophobic macromonomers can be synthesized using standard synthetic procedures which involve polymerzing, usually under cationic or anionic initiation conditions, the appropriate monomer unit, (e.g., isobutylene, 1,3-butadiene, isoprene etc.). A wide variety of initiating systems can be used, nonlimiting examples of which include cationic initiators, such as cumyl acetate/$TiCl_4$, cumyl methyl ether/$BCl_3$; and anionic initiators such as n-butyl lithium, sec-butyl lithium, t-butyl lithium, lithium aluminum hydride, sodium hydride, and the like. Nonlimiting examples of these initiating systems are provided in Designed Polymers by *Carbocationic Macromolecular Engineering, Theory and Practice*, J. P. Kennedy and B. Ivan, Chapter II, p.5, Hanser Publishers, N.Y. (1991), and in *Anionic Polymerization: Principles and Practice*, Maurice Morton, Chapter 2, p. 13, Academic Press, N.Y. (1983).

In the case of cationic polymerization, once the desired degree of polymerization is complete the polymer is isolated and further derivatized to obtain vinyl benzyl, methacryloyl or acryloyl end capped polymer. A nonlimiting example of a macromonomer synthesized by cationic polymerization is poly(isobutylene). In the case of anionic polymerization, once the desired degree of polymerization is achieved, an appropriate endcapping reagent is typically used to terminate the polymerization and to endcap the macromonomer. Nonlimiting examples of these endcapping reagents include 2-vinylbenzyl chloride, 3-vinylbenzyl chloride, 4-vinylbenzyl chloride, and the like. Alternatively, the endcapping can be achieved by reacting the polymeric reaction mixture with one equivalent of ethylene oxide to terminate the polymer with a —$CH_2CH_2$—O— moiety, followed by reaction with an endcapping reagent such as an unsaturated acid halide.

Preferred Polymers of the Present Invention

Particularly preferred polymers for use in the present invention include the following (the weight percents below refer to the amount of reactants added in the polymerization reaction, not necessarily the amount in the finished polymer):

(i) Poly[poly(tert-butylacrylate)-graft-poly(isobutylene) macromonomer] (80/20 w/w); total graft copolymer weight avenge molecular weight of 100,000; macromonomer weight average molecular weight 5000.

(ii) Poly[poly(4-tert-butylstyrene)-graft-poly (isobutylene) macromonomer] (70/30 w/w); total graft copolymer weight avenge molecular weight of 150,000; macromonomer weight avenge molecular weight 3000.

(iii) Poly[(4-tert-butylstyrene)-graft-poly(2-ethylhexyl methacrylate) macromonomer] (80/20 w/w); total graft copolymer weight average molecular weight of 150,000; macromonomer weight average molecular weight 10,000.

(iv) Poly[(tert-butylacrylate-co-styrene)-graft-poly (isobutylene)] (60/20/20 w/w/w);total graft copolymer weight average molecular weight of 100,000; macromonomer weight average molecular weight 5000.

Synthesis of the Graft Copolymers

The graft copolymers can be made by free radical polymerization of the A monomers with the B macromonomers. It is not intended to necessarily exclude from this invention any copolymers made by means other than free radical polymerization, so long as the product has the desired physical properties. The copolymers herein are formed from randomly repeating A monomer units, and B macromonomer units.

The general principles of free radical polymerization methods are well understood. See, for example, Odian, "Principles of Polymerization", 2nd edition, John Wiley & Sons, 1981, pp. 179–318. The desired monomers and macromonomers are all placed in a reactor, along with a sufficient amount of a mutual solvent so that when the reaction is complete the viscosity of the reaction is reasonable. Typical monomer and macromonomer loadings are from about 10% to about 50%, on a weight basis. Undesired terminators, especially oxygen, can be removed as needed. This is done by evacuation or by purging with an inert gas, such as argon or nitrogen. The initiator is introduced and the reaction brought to the temperature needed for initiation to occur, assuming thermal initiators are used. Nonlimiting examples of suitable initiators include those selected from the group consisting of azo initiators, peroxide initiators, redox initiators, and photochemical initiators. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as needed utilizing a variety of techniques including filtration, extraction, membrane separation, gel permeation chromatography, and the like.

There are numerous variations on these procedures which are entirely up to the discretion of the synthetic chemist (e.g., choice of degassing method and gas, choice of initiator type, extent of conversion, reaction loading, etc). The choice of initiator and solvent are often determined by the requirements of the particular monomers and macromonomer used, because different monomers and macromonomers have different solubilities and different reactivities to a specific initiator.

The copolymers of the present invention can also be synthesized by first preparing a reactive, intermediary polymer from A monomer units, followed by further polymerization of the resulting intermediary copolymer with suitable monomers to form the hydrophobic side chains.

Analysis of the graft copolymer reaction product and the extracted materials, and the purified graft copolymer can be performed by conventional analysis techniques known in the art. These include, for example, nuclear magnetic resource (NMR), infrared molecular spectroscopies, gel permeation/size exclusion chromatography, membrane osmometry, and atomic absorption and emission spectroscopies.

Solvent For The Graft Copolymer

The compositions of the present invention comprise a hydrophobic, volatile, liquid which is a solvent for the graft copolymers of the present invention. Suitable solvents are selected from hydrophobic, volatile branched chain hydrocarbons, silicones and combinations thereof.

In general, the present compositions will comprise from about 0.1% to about 75%, preferably from about 0.2% to about 25%, and more preferably from about 0.5% to about 15%, of the solvent. The weight ratio of linear copolymer to solvent is generally from about 1:100 to about 5:1, preferably from about 1:10 to about 1:1, more preferably from about 1:8 to about 2:3.

The hydrophobic, volatile solvent exhibits a significant vapor pressure at ambient conditions (e.g., 1 atmosphere, 25° C.), as is understood by those in the art. As used herein, the term "volatile" refers to solvents having a boiling point at one atmosphere of 260° C. or less, preferably 250° C. or less, more preferably 230° C. or less, most preferably 225° C. or less. In addition, the boiling point or the hydrophobic, volatile solvent will generally be at least about 50° C., preferably at least about 100° C. The term "nonvolatile", on the other hand, shall refer to solvents which have a boiling point at one atmosphere of greater than 260° C. The solvent should also be acceptable for topical application to the hair and skin (i.e., no undue irritation, sensitization or other reactions are induced by the solvent).

The graft copolymer is soluble in the hydrophobic, volatile solvent in the present compositions. In general, the copolymer should be soluble at 25° C. at a concentration of 0.1% by weight of the solvent, preferably at 1%, more preferably at 5%, most preferably at 15%.

The hydrophobic, volatile solvent, however, is insoluble in aqueous carriers of the composition. This is determined in the absence of the copolymer, or other emulsifying agents, and can easily be verified by observing whether the solvent and aqueous carrier form separate phases after being mixed together at room temperature (as viewed without magnification).

Preferred hydrophobic, volatile branched chain hydrocarbons useful as the solvent herein contain from about 10 to about 16, more preferably from about 12 to about 16, most preferably from about 12 to about 14 carbon atoms. (E.g., preferred branched chain hydrocarbons include $C_{10}$–$C_{16}$ branched chain hydrocarbons, $C_{11}$–$C_{14}$ branched chain hydrocarbons, and $C_{12}$ branched chain hydrocarbons). Saturated hydrocarbons are preferred, although it is not intended to exclude unsaturated hydrocarbons. Examples of such preferred branched chain hydrocarbons include isoparaffins of the above chain sizes. Isoparaffins are commercially available from Exxon Chemical Co.; examples include Isopar™ and K ($C_{11}$–$C_{12}$ isoparaffins), and Isopar™ ($C_{11}$–$C_{13}$ isoparaffins). Other suitable branched chain hydrocarbons are isododecane and isohexadecane. Isododecane is preferred and is commercially available from Preperse, Inc. (South Plainfield, N.J., U.S.A.) as Permethyl™ 99A.

Preferred silicones useful as the hydrophobic, volatile solvent herein include hydrophobic, volatile siloxanes (such as phenyl pentamethyl disiloxane, phenylethyl pentamethyl disiloxane, hexamethyl disiloxane, methox3propyl heptamethyl cyclotetrasiloxane, chloropropyl pentamethyl disiloxane, hydroxypropyl pentamethyl disiloxane, cyclomethicones, including octamethyl cyclotetrasiloxane and decamethyl cyclopentasiloxane), and mixtures thereof. Preferred solvents are cyclomethicones, more preferably octamethyl cyclotetrasiloxane and decamethyl cyclopentasiloxane.

Hair Care Compositions

The compositions of the present invention also comprise a suitable carrier or hair care matrix for delivering the graft copolymer and the hydrophobic, volatile solvent to the hair. Any carrier suitable for delivery of the copolymer/hydrocarbon solvent to the hair can be used. The carrier can comprise a volatile liquid which is water or is otherwise water soluble, or a mixture thereof and in which the volatile solvent of the copolymer is not soluble. In general, the compositions will comprise from about 50% to about 99.3%, preferably from about 70% to about 99%, more preferably from about 85% to about 98%, of carrier or hair care matrix.

The carrier liquid herein can include water or other hydrophilic fluids, and combinations thereof. Suitable carrier fluids for use in the present invention, in addition to water, include lower alcohols ($C_1$–$C_4$ alcohols, preferably $C_2$–$C_4$ alcohols such as ethanol and isopropanol) and mixtures of lower alcohols. Preferred solvents include water, ethanol, and mixtures thereof. Especially preferred is water.

The preferred compositions are in the form of a discontinuous phase of dispersed droplets, or particles, of the copolymer and the hydrophobic volatile solvent distributed throughout the carrier. The carrier can also comprise a variety of other components, such as other active ingredients, theology modifiers such as thickeners, gelling agents, etc. The compositions of the present invention can be in the form of liquids, lotions, creams gels, etc.

The carrier may include gel vehicle materials or other rheology modifiers. These are particularly contemplated for use in products such as hair rinses, shampoos, mousses, and creams and lotions.

Gel vehicles can comprise two essential components: a lipid vehicle material and a surfactant vehicle material. Gel vehicles are generally described in the following documents: Barry, "The Self Bodying Action of the Mixed Emulsifier Sodium Dodecyl Sulfate/Cetyl Alcohol", 28 J. of Colloid and Interface Science 82–91 (1968); Barry, et al., "The Self-Bodying Action of Alkyltrimethylammonium Bromides/Cetostearyl Alcohol Mixed Emulsifiers; Influence of Quaternary Chain Length", 35 J. of Colloid and Interface Science 689–708 (1971); and Barry, et al., "Rheology of Systems Containing Cetomacrogol 1000—Cetostearyl Alcohol, I. Self Bodying Action", 38 J. of Colloid and Interface Science 616–625 (1972).

The carrier may incorporate one or more lipid vehicle materials which are essentially water-insoluble, and which contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Lipid vehicle materials among those useful herein are disclosed in *Bailey's Industrial Oil and Fat Products*, (3rd edition, D. Swern, ed., 1979). Fatty alcohols included among those useful herein are disclosed in the following documents: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et at., issued May 26, 1981; British Specification 1,532,585, published Nov. 15, 1978; and Fuku Shima, et al., "The Effect of Cetostearyl Alcohol in Cosmetic Emulsions", 98 *Cosmetics & Toiletties* 89–112 (1983). Fatty esters included among those useful herein are disclosed in U.S. Pat. No. 3,341,465, Kaufman, et al., issued Sep. 12, 1976. If included in the compositions of the present invention, the lipid vehicle material is typically present at from about 0.1% to about 10.0% of the composition; the cationic surfactant vehicle material is present at from about 0.05% to about 5.0% of the composition.

Cationic surfactant materials are suitable for use in the gel vehicles, and include, but are not limited to, those described in detail below. The compositions hereof can also contain a lipid vehicle without the inclusion of a cationic surfactant.

The use of nonionic cellulose ethers and water-soluble gums for thickening compositions is also contemplated. See for example, U.S. Pat. No. 4,557,928, Glover, issued Dec. 10, 1985, teaching a hair conditioner comprising a suspension system which consists of one of glueart gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum.

Nonionic water-soluble cellulose ethers are preferred polymers that can be employed in hair care compositions. Cellulose ethers are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.). Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Other carrier ingredients for use in the compositions of the present invention, especially for hair rinses, include combinations of one or more nonionic, water soluble polymeric materials that have been hydrophobically-modified (hereinafter alternatively referred to as "hydrophobically modified nonionic water-soluble polymer"), with one or more surfactants, such as quaternary ammonium compounds (such as ditallowdimethyl ammonium chloride). These vehicles are described in detail in the following patents: U.S. Pat. No. 5,106,609, issued Apr. 21, 1992 to Bolich et al., U.S. Pat. No. 5,100,658, issued Mar. 31, 1992 to Bolich et al., U.S. Pat. No. 5,104,646, issued Apr. 14, 1992 to Bolich et al, and U.S. Pat. No. 5,100,657, issued Mar. 31, 1992 to Pansher-Jackson et at.

These systems provide a gel-like rheology without necessarily being gels in the technical sense. When such systems are used to thicken the present compositions, from about 0.3% to about 5.0%, preferably from about 0.4% to about 3.0%, of the hydrophobically modified nonionic water-soluble polymer is preferably utilized with from about 0.3% to about 5.0%, preferably from about 0.4% to about 3.0%, of a water-soluble polymeric thickening material such as described herein.

By "hydrophobically modified nonionic water-soluble polymer" is meant a nonionic water-soluble polymer which has been modified by the substitution with a sufficient amount of hydrophobic groups to make the polymer less soluble in water. By "water-soluble" what is meant is the polymer or salt, thereof, constituting the polymer backbone of the thickener should be sufficiently soluble such that it forms a substantially clear solution when dissolved in water at a level of 1%, by weight of the solution, at 25° C.

The polymer backbone of the hydrophobically modified nonionic water-soluble polymer can be essentially any water-soluble polymer. Examples of water soluble polymers useful for forming the hydrophobically modified nonionic water-soluble polymer include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone, dextrans, for example Dextran purified crude Grade 2P, available from D&O Chemicals, plant exudates such as acacia, ghatti, and tragacanth, seaweed extracts such as sodium alginate, propylene glycol alginate, sodium carrageenan, cationic polymers such as Ucare JR-polymer (a cationic modified hydroxyethyl cellulose available from Union Carbide), natural polysaccharide materials, such as guar gum, locust bean gum, and xanthan gum. Nonionic water-soluble cellulose ethers are preferred to be employed as the polymer substrate of such hydrophobically modified polymers. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The hydrophobic groups which modify the nonionic water-soluble polymer can be $C_8$ to $C_{22}$ alkyl, aryl alkyl, alkyl aryl groups and mixtures thereof. One or more hydrophobic groups can be attached to the cellulose ether substrate via an ether, ester or urethane linkage. The ether linkage is preferred.

The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1. One commercially available hydrophobically modified nonionic water-soluble polymer material which meets the foregoing requirements is NATROSOL PLUS Grade 430, hydrophobically modified hydroxyethylcellulose available from Aqualon Company, Wilmington, Del. This material has a $C_{16}$ alkyl substitution of about 0.5% to about 0.9% by weight. The hydroxyethyl molar substitution for this material is from about 2.8 to about 3.2. The average molecular weight for the water-soluble cellulose prior to modification is approximately 300,000.

Another material of this type is sold under the trade name NATROSOL PLUS CS Grade D-67, by Aqualon Company, Wilmington, Del. This material has a $C_{16}$ alkyl substitution of from about 0.50% to about 0.95%, by weight. The hydroxyethyl molar substitution for this material is from about 2.3 to about 3.3. The average molecular weight for the water-soluble cellulose prior to modification is approximately 700,000.

The hydrophobically modified nonionic water-soluble polymer can be used in combination with water soluble or water insoluble surfactants.

In this regard, "water-soluble surfactant" means surfactant materials which form substantially clear, isotropic solutions when dissolved in water at 0.2 weight percent at 25° C. The water-soluble surfactant preferably has a molecular weight of less than about 20,000.

Essentially any water-soluble surfactant material which meets these requirements will work in the present invention. However, the following materials have been found to be particularly preferred: cetyl betaine, ammonium lauryl sulfate, ammonium laureth sulfate, cetyl trimethyl ammonium chloride, and mixtures thereof.

When such systems are used to thicken the present compositions, from about 0.1% to about 10.0%, preferably from about 0.2% to about 5.0%, of the hydrophobically-modified nonionic water soluble polymer is generally utilized with from about 0.02% to about 0.30%, preferably from about 0.05% to about 0.30%, most preferably from about 0.05% to about 0.20%, of the water-soluble surfactant. The water-soluble surfactant level is kept low because higher levels of water-soluble surfactants interfere with the hydrophobically-modified hydroxyethyl cellulose thickener and produce compositions with much less desirable rheologies.

By "water-insoluble surfactant" for use in such systems it is meant surfactant materials which do not form substantially clear isotropic solutions when dissolved in water at greater than 0.2 weight percent at 25° C. The water-insoluble surfactant preferably has a molecular weight of less than about 20,000. Essentially any water-insoluble surfactant material which meets these requirements will work in the present invention, however, water-insoluble cationic surfactant materials are preferred. Cationic surfactants are described below. The following nonexclusive materials are suitable: stearamide diethanolamine (stearamide DEA), cocoamide methanolamine (cocoamide MEA), dimethyl stearamine oxide, glyceryl monooleate, sucrose stearate, PEG-2 stearamine, polyethylene glycol ethers of fatty alcohols, such as Cetheth-2 of the formula $CH_3-(CH_2)_{14}-CH_2-(OCH_2CH_2)_n-OH$, where n has an average value of 2 (commercially available under the trade name Brij 56 from ICI Americas), glycerol stearate oilrate, dihydrogenated tallow dimethyl ammonium chloride, polyoxyethylene, polyoxypropylene block polymers such as Poloxamer 181, of the formula:

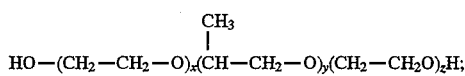

wherein on average x=3, y=30 and z=3 (commercially available from BASF Wyandotte under the trade name Pluronic L-61), hydrogenated tallow dimethyl betaine, and hydrogenated tallow amide DEA.

When such systems are used to thicken the present compositions, from about 0.1% to about 10.0%, preferably from about 0.2% to about 5.0%, of the hydrophobically-modified nonionic polymer is generally utilized with from about 0.02% to about 10.0%, preferably from about 0.05% to about 3.0%, most preferably from about 0.05% to about 2.0%, of the water-insoluble surfactant.

Cationic surfactants useful in the compositions of the present invention, including the gel vehicle systems as well as hydrophobically modified nonionic polymer systems, include those containing amino or quaternary ammonium hydrophilic moieties which are positively charged when dissolved in the aqueous composition of the present invention. Cationic surfactants among those useful herein are disclosed in more detail below.

It is also contemplated to utilize a suspending agent to thicken the compositions and/or to suspend the copolymer branched hydrocarbon solvent phase in the carrier. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. 4,741,855, Grote et al., issued May 3, 1988. Especially preferred is ethylene glycol distearate.

Also included among the long chain acyl derivatives useful as suspending agents are the N,N-di(hydrogenated) $C_8$–$C_{22}$ (preferably $C_{12}$–$C_{22}$, more preferably $C_{16}$–$C_{18}$) amido benzoic acid, or soluble salt (e.g., K, Na salts) thereof particularly N,N-di(hydrogenated)tallow amido benzoic acid which is commercially marketed by Stepan Company (Northfiled, Ill., U.S.A.).

Surfactants

Surfactants are optional ingredients in the compositions of the invention, particularly shampoo and conditioner compositions. When present, the surfactant typically comprises from about 0.05% to about 50% of the composition. For a shampoo, the level is preferably from about 10% to about 30%, most preferably from about 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants.

Synthetic anionic detergents useful herein, particularly for shampoo compositions, include alkyl and alkyl ether sulfates. These materials typically have the respective formulae $ROSO_3M$ and $RO(C_2H_4O)xSO_3M$, wherein R is alkyl or alkenyl of from about 10 to about 20 carbon atoms, x is 1 to 10, and M is a water-soluble cation such as ammonium, sodium, potassium and triethanolamine.

Another suitable class of anionic surfactants are the water-soluble salts of the organic, sulfuric acid reaction products of the general formula:

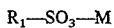

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The α-olefins from which the olefin sulfonates are derived are mono-olefins having about 12 to about 24 carbon atoms, preferably about 14 to about 16 carbon atoms. Another class of anionic organic surfactants are the β-alkyloxy alkane sulfonates. These compounds have the following formula:

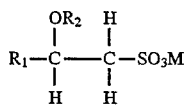

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described. Many additional nonsoap synthetic anionic surfactants are described in McCutcheon's, Detergents and Emulsifiers, 1984 Annual, published by Allured Publishing Corporation.

Also U.S. Pat. No. 3,929,678, Laughlin et at., issued Dec. 30, 1975, discloses many other anionic as well as other surfactant types.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. Those derived from the condensation of ethylene oxide with the product resulting from the reaction of propylene oxide and ethylene diamine products.
2. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.
3. Long chain tertiary amine oxides such as those corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals (the arrow in the formula is a conventional representation of a semipolar bend).

4. Long chain tertiary phosphine oxides corresponding to the following general formula:

wherein R contains an alkyl, alkenyl or monohydroxyalkyl radical ranging from about 8 to about 18 carbon atoms in chain length, from 0 to about i0 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond.

5. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetra decyl methyl sulfoxide, 3-methoxytridecyl methyl sulfoxide, 3-hydroxytridecyl methyl surfoxide, 3-hydroxy-4-dodecoxybutyl methyl surfoxide.

Cationic surfactants useful in compositions of the present invention, particularly the conditioner compositions, include those containing amino or quaternary ammonium hydrophilic moieties which are positively charged when dissolved in the aqueous composition of the present invention. Cationic surfactants among those useful herein are disclosed in the following documents: M. C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Among the quaternary ammonium-containing cationic surfactant materials useful herein are those of the general formula:

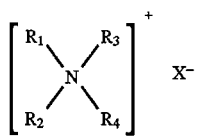

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, eg., those of about 12 carbons, or higher, can be saturated or unsaturated.

Other quaternary ammonium salts useful herein are diquaternary ammonium salts, such as tallow propane diammonium dichloride.

Quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chlorides, di(hydrogenated tallow) dimethyl ammonium chloride, dioctadecyl dimethyl ammonium chloride, dieocosyol dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(saturated or unsaturated tallow) dimethyl ammonium chloride is a particularly preferred quaternary ammonium salt.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981.

Zwitterionic surfactants, useful in shampoos as well as conditioners, are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

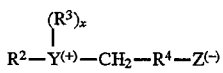

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphors, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as coco dimethyl carboxymethyl betaine, lauryl dimethyl carboxymethyl betaine, lauryl dimethyl alpha carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hy droxyethyl) sulfopropyl betaine and the like; amidobetaines and amidosulfobetaines, wherein the $RCONH(CH_2)_3$ radical is attached to the nitrogen atom of the betaine are also useful in this invention.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylamino propane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Silicone Hair Conditioning Agent

An optional component of the present invention is a nonvolatile, silicone conditioning agent which is not soluble in the aqueous or water soluble phase of compositions wherein the carrier is aqueous-based or otherwise based on water soluble solvents.

The silicone hair conditioning agent for use herein will preferably have an average viscosity of from about 1,000 to about 20,000,000 centistokes at 25° C., more preferably from about 10,000 to about 10,000,000, even more preferably from about 100,000 to about 5,000,000. The viscosity of silicones herein can, in general, be measured by means of a glass capillary viscometer as set forth in Dow Coming Corporate Test Method CTM0004, Jul. 20, 1970.

The silicone hair conditioning agent will typically be used in the shampoo compositions hereof at levels of from about 0.05% to about 10% by weight of the composition, preferably from about 0.1% to about 10%, more preferably from about 0.5% to about 8%, most preferably from about 0.5% to about 5%.

Suitable nonvolatile silicone fluids include polyalkyl siloxanes, polyaryl siloxanes, polyalkyl siloxanes, polyether siloxane copolymers, and mixtures thereof. Other insoluble, nonvolatile silicone fluids having hair conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000.

Silicone fluids hereof also include polyalkyl or polyaryl siloxanes with the following structure:

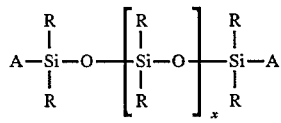

wherein R is alkyl or aryl, and x is an integer from about 1 to about 8,000 may be used, preferably from about 5 to about 8,000. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their Viscasil$^R$ and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556° Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Cationic Polymer Hair Conditioning Agent

The compositions of the present invention can also comprise a water soluble, cationic organic polymer conditioning agent for hair. The polymeric cationic conditioning agent hereof will generally be present at levels of from about 0.05% to about 5%, preferably from about 0.1% to about 4%, more preferably from about 0.2% to about 3%, by weight, of the shampoo composition. By "water soluble" cationic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

The cationic organic polymers useful in the hair conditioning agent hereof are organic polymers that can provide conditioning benefits to hair and that are soluble in the shampoo composition. Any cationic polymers which can provide these benefits can be used. As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will have cationic nitrogen-containing moieties such as quaternary ammonium or cationic amino moieties, or a mixture thereof.

The cationic charge density is preferably at least about 0.9 meq/gram, more preferably at least about 1.0 meq/gram, even more preferably at least abut 1.1 meq/gram, most preferably at least about 1.2 meq/gram. The cationic charge density is preferably no greater than about 4 meq/gram, more preferably no greater than about 3.0 meq/gram, most preferably no greater than about 2.0 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use, which will in general be from about pH 3 to about pH 9, most generally from about pH 4 to about pH 8.

Any anionic counterions can be utilized for the cationic polymers so long as the water solubility criteria is met. Suitable counterions include halides (e.g., Cl—, Br—, I—, or F—, preferably Cl—, Br—, or I—), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be convened to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an action which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkyl-aminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A.) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., U.S.A.); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256.

Other cationic polymers that can be used include polysaccharide polymers, such as cationic cellulose derivatives and cationic starch derivatives.

Cationic polysaccharide polymer materials suitable for use herein include those of the formula:

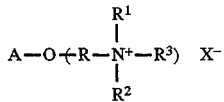

wherein:

A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N. J., U.S.A.) in their Polymer JR$^R$ and LR$^R$ series of polymers, as salts of hydroxyethyl cellulose reacted with trimethyl ammonium substituted epoxide, referred to in the industry (CTFA) as Polyquaternium 10. Another type of cationic. cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., U.S.A.) under the tradename Polymer LM-200.

Other cationic polymers that can be used include cationic guar gum derivatives, such as guar hydroxypropyltrimonium chloride (commercially available from Celanese Corp. in their Jaguar$^R$ series). Other materials include quaternary nitrogen-containing cellulose ethers (e.g., as described in U.S. Pat. No. 3,962,418), and copolymers of etherified cellulose and starch (e.g., as described in U.S. Pat. No. 3,958,581).

Organic Oil Conditioning Agents

The compositions of the present invention can also comprise a nonvolatile, water insoluble, organic, oil as a conditioning agent for hair. The hair conditioning oily liquid can add shine and luster to the hair. The conditioning oil is typically present in the compositions at a level of from about 0.05% to about 5%, by weight of the composition, preferably from about 0.2% to about 3%, more preferably from about 0.5% to about 1%.

By "nonvolatile" what is meant is that the oily material exhibits very low or no significant vapor pressure at ambient conditions (e.g., 1 atmosphere, 25° C.), as is understood in the art. The nonvolatile oily materials preferably have a boiling point at ambient pressure of about 260° C. or higher.

By "water insoluble" what is meant is that the oily liquid is not soluble in water (distilled or equivalent) at a concentration of 0.1%, at 25° C.

The conditioning oil hereof generally will have a viscosity of about 3 million cs or less, preferably about 2 million cs or less, more preferably about 1.5 million cs or less.

The conditioning oils hereof are liquids selected from the group consisting of hydrocarbon oils and fatty esters. The fatty esters hereof are characterized by having at least 10 carbon atoms, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain more than 16 carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be at least about 400, preferably at least about 500, more preferably at least about 600. Specific examples of suitable materials include paraffin oil, mineral oil, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of eicosane, such as 2, 2, 4, 4, 6, 6, 8, 8–10-nonylmethylundecane, sold by Permethyl Corporation. A preferred hydrocarbon polymer is polybutene, such as the copolymer of isobutylene and butene. A commercially available material of this type is L-14 polybutene from Amoco Chemical Co. (Chicago, Ill., U.S.A.).

Monocarboxylic acid esters hereof include esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific examples include isocetyl stearyol stearate, diisopropyl adipate, and tristearyl citrate.

Polyhydric alcohol esters include alkylene glycol esters, for example ethylene glycol mono and di-fatty acid esters, diethylene glycol mono- and di-fatty acid esters, polyethylene glycol mono-and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain cathoxylic acids, such as $C_{10}$–$C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Preferred glycerides are di-, and tri-glycerides. Especially preferred are triglycerides.

The compositions herein can contain a variety of other optional components suitable for rendering such compositions more cosmetically or aesthetically acceptable or to provide them with additional usage benefits, e.g. medicinal benefits. Such conventional optional ingredients are well-known to those skilled in the art, e.g., sunscreens, medicaments (e.g. anti-bacterials, anti-inflamatories, anti-acne actives, etc.), colors and dyes, perfumes, pearlescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and polymer plasticizing agents, such as glycerin, diisobutyl adipate, butyl stearate, and propylene glycol. Such optional ingredients generally are used individually at levels of from about 0.01% to about 10.0%, preferably from about 0.05% to about 5.0%, of the composition.

The pH of the present compositions generally will be between about 3 and about 9, preferably between about 4 and about 8.

As with all compositions, the present invention should not contain components which unduly interfere with the performance of the compositions.

The hair care compositions of the present invention can be made using conventional formulation and mixing techniques. Methods of making various types of cosmetic compositions are described more specifically in the following examples.

Method of Using Hair Care Compositions

The hair care compositions of the present invention are used in conventional ways to provide the desired benefit appropriate to the product such as hair styling, holding, cleansing, conditioning and the like for hair care compositions. Such methods of use depend upon the type of composition employed but generally involve application of an effective amount of the product to the hair, which may then be rinsed from the hair (as in the case of shampoos and some conditioning products) or allowed to remain on the hair (as in the case of spray, mousse, or gel products). By "effective amount" is meant an amount sufficient to provide the benefit desired. Preferably, hair rinse, mousse, and gel products are applied to wet or damp hair prior to drying and styling of the hair. After such compositions are applied to the hair, the hair is dried and styled in the usual ways of the user. Hair sprays are typically applied to dry hair after it has already been dried and styled.

The following examples further illustrate preferred embodiments within the scope of the present invention. The examples are given solely for the purposes of illustration and are not to be construed as limitations of the present invention as many variations of the invention are possible without departing from its spirit and scope.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Example 1

Synthesis of Acryloyl Encapped Polyisobutylene Macromonomer

Prepare hydroxyl endcapped polyisobutylene polymer (PIB-OH) having a weight average molecular weight of about 4,172 g/mol by conventional living carbocationic polymerization of isobutylene (for example, as described in G. Kaszas, Poly. Bull., 20, 413 (1989). Prepare a solution of 100 grams (0.024 mol) of the (PIB-OH) in 300 grams dry methylene chloride. Add a two fold mole excess (4.84 g, 0.048 mol) triethylamine to the solution. Add this solution dropwise to a solution of acryloyl chloride (4.35 g, 0.048 m) in dry methylene chloride (100 g) at 0° C. Stir for about 12 hours at room temperature, filter the mixture and evaporate the excess triethylamine and methylene chloride to obtain acryloyl endcapped polyisobutylene macromonomer.

Example 2

(i) Synthesis of Poly(tert-butyl acrylate)-graft-[poly(isobutylene) macremonomer] (80/20 w/w); total graft copolymer weight average molecular weight of 100,000; macromonomer weight average molecular weight 5000.

To a solution of 20.0 grams of acryloyl endcapped poly(isobutylene) macromonomer of Example 1, and 80 grams of tert-butyl acrylate in 500 mL of tetrahydrofuran, add 0.5 grams of azoisobutryonitire (AIBN) initiator. Reflux the resulting solution for about 20 hours, then quench the reaction by the addition of about 5 mL of methanol. Pour the solution into a teflon pan and evaporate the tetrahydrofuran at room temperature under a fume hood. Redissolve the resulting polymer film in THF and precipitate in water. Dry the resulting polymer in a vacuum oven.

Alternatively, by varying the monomers and macremoners used, this general procedure is used to prepare other copolymers of the present invention:

(ii) Poly(4-tert-butyl styrene)-graft-[poly(isobutylene) macromonomer] (70/30 w/w); total polymer weight average molecular weight of 150,000; macromonomer weight average molecular weight 3000.

(iii) Poly[(4-tert-butyl styrene)-graft-poly(2-ethylhexyl methacrylate) macromonomer] (80/20 w/w); total polymer weight average molecular weight of 150,000; macromonomer weight average molecular weight 10,000.

(iv) Poly[(tert-butyl acrylate-co-styrene)-graft-poly(isobutylene) macromonomer] (60/20/20 w/w/w); total polymer weight average molecular weight of 100,000; macremonomer weight average molecular weight 5000.

Examples 3–5

The following hair styling/conditioning rinse compositions are representative of the present invention.

| Composition | 3 wt. % | 4 wt. % | 5 wt. % |
|---|---|---|---|
| Conditioner Premix | | | |
| Water | q.s. | q.s. | q.s. |
| Citric Acid | 0.02 | 0.02 | 0.02 |
| Sodium Citrate | 0.09 | 0.09 | 0.10 |
| Cetyl Alcohol | 0.12 | 0.12 | 0.12 |
| Stearyl Alcohol | 0.08 | 0.08 | 0.08 |
| Natrosol Plus CS Grade D-67[1] | 1.02 | 1.00 | 0.99 |
| Xanthan Gum[2] | 0.25 | 0.25 | 0.25 |
| Styling Polymer Premix | | | |
| Graft Copolymer from Example 2(i) | 1.75 | 1.75 | 1.75 |
| Permethyl 99A | 8.54 | 8.54 | 8.54 |
| Trimethylsiloxysilicate | 0.11 | 0.11 | 0 |
| Kathon CG | 0.03 | 0.03 | 0.03 |
| Perfume | 0.33 | 0.33 | 0.33 |
| Silicone Premix | | | |
| DRO Water | 9.48 | 9.48 | 8.57 |
| Adogen 470[4] | 0.70 | 0.60 | 0.93 |
| Adogen 471[5] | 0.05 | 0.15 | 0.07 |
| Decamethyl cyclopentasiloxane/ Polydimethyl Siloxane Gum[3] | 1.67 | 1.67 | 2.33 |
| Trimethylsilyl Amodimethicone (Dow Corning Q2-8220) | 0.10 | 0.10 | 0.10 |
| Surfactant Premix | | | |
| DRO Water | 5.70 | 5.70 | 5.70 |
| Stearalkonium Chloride | 0.30 | 0.30 | 0.30 |

[1]Hydrophobically modified hydroxyethyl cellulose from Aqualon Corp.
[2]Readily dispersible xantham gum
[3]SE-76 gum available From General Electric
[4]Ditallow dimethyl ammonium chloride, Sherex Chemical Co., Dublin, Ohio, USA; 75% aqueous solution
[5]Tallow trimethyl ammonium chloride, Sherex Chemical Co.; 50% aqueous solution.

Prepare the silicone premix by combining and mixing (in a separate vessel) water, Adogen 470 and Adogen 471 at 85° C. Cool to 71° C. and add the silicone gum/decamethyl cyclopentasiloxane solution and Amodimethicone; mix until homogeneous. Cool to 38° C. while using homogenizer (such as Tekmar).

Prepare the surfactant premix by combining and mixing (in a separate vessel) water and Stearalkonium Chloride at 38° C.

Prepare the conditioner premix by combining and mixing (in a separate vessel) the DRO water heated to 71° C., adding the Citric acid, sodium citrate, cetyl alcohol, stearyl alcohol and Natrosol Plus CS grade D-67, and mixing until homogeneous. Add the xanthan gum and mix until homogeneous.

Prepare the styling polymer premix by combining and mixing (in a separate vessel) the graft copolymer, Permethyl 99A, and Trimethylsiloxysilicate until homogeneous.

Combine and mix the styling polymer premix, Kathon CG and perfume until homogeneous. Further disperse the mixture with an in-line homogenizer (such as Tekmar homogenizer) and then cool the mixture to 38° C. Complete the conditioner by adding the conditioner premix, the silicone premix and the surfactant premix at 38° C. Mix until homogeneous, then cool the composition to 25° C.

Apply the compositions defined in Examples 3–5 to the hair in the conventional manner to provide effective hair conditioning and styling/hold benefits without leaving the hair with a sticky/stiff feel.

Example 6

Polymer Premix with Added Drying Aid

Prepare the following polymer premix utilizing conventional mixing techniques.

| Ingredients | Weight % |
| --- | --- |
| Graft Copolymer from Example 2(ii) | 16.83 |
| Permethyl 99A | 83.17 |
| Trimethylsiloxysilicate | 1.00 |

Prepare the polymer premix by adding the graft copolymer to the Permethyl 99A while mixing. Heat to 80°–84° C. in a covered vessel, maintaining mixing. Cool to 23°–27° C. and add trimethylsiloxysilicate while mixing.

Example 7

Polymer Premix with Added Drying Aid

Prepare the following polymer premix utilizing conventional mixing techniques.

| Ingredients | Weight % |
| --- | --- |
| Graft Copolymer from example 2(iv) | 15.00 |
| Isododecane | 83.50 |
| Polydimethylsiloxane | 1.50 |

(Dow Corning, Dow Corning 200 Fluid (20 csk))

Prepare the polymer premix by adding the graft copolymer to the isododecane while mixing. Heat to 80°–84° C. in a covered vessel, maintaining mixing. Cool to 23°–27° C. and add polydimethylsiloxane while mixing.

Example 8

Hair Conditioner

Prepare a rinse-off hair conditioner composition from the following components utilizing conventional mixing techniques.

| Ingredient | Weight % A | Weight % B |
| --- | --- | --- |
| Styling Agent Premix | | |
| Copolymer Premix of Example 7[1] | 10.00 | 10.00 |
| Silicone Premix | | |
| Silicone gum, GE SE76[2] | 0.30 | 0.30 |
| Octamethyl cyclotetrasiloxane | 1.70 | 1.70 |
| Main Mix | | |
| Water | QS 100 | QS 100 |
| Cetyl Alcohol | 1.00 | — |
| Quaternium 18[3] | 0.85 | 0.85 |
| Stearyl Alcohol | 0.70 | — |
| Hydroxyethyl Cellulose | 0.50 | — |
| Cetyl Hydroxythyl Cellulose[4] | — | 1.25 |
| Ceteareth-20 | 0.35 | — |
| Fragrance | 0.20 | 0.20 |
| Dimethicone copolyol | 0.20 | — |
| Citric Acid | 0.13 | 0.13 |
| Methylchloroisothiazolinone (and) methylisothiazolinone | 0.04 | 0.04 |
| Sodium Chloride | 0.01 | 0.01 |
| Xanthan Gum | — | 0.20 |

Prepare the conditioner by first comixing all the Main Mix ingredients, heating to about 60° C. with mixing. Cool the mixure to about 45° C. with colloid milling (Example A) or mixing (Example B). At this temperature, add the two premixes separately with moderate agitation. Allow the resulting conditioner to cool to room temperature.
[1] Alternatively, conditioner compositions are prepared with polymer premixes from Example 2(ii) and 2(iii).
[2] Commercially available from General Electric.
[3] Dimethyl Di(Hydrogenated Tallow) Ammonium Chloride
[4] Commercially available as Polysurf D-67 from Aqualon.

Prepare the conditioner by first comixing all the Main Mix ingredients, heating to about 60° C. with mixing. Cool the mixture to about 45° C. with colloid milling (Example A) or mixing (Example B). At this temperature, add the two premixes separately with moderate agitation. Allow the resulting conditioner to cool to room temperature.

1 Alternatively, conditioner compositions are prepared with polymer premixes from Example 2(ii) and 2(iii).

2 Commercially available from General Electric.

3 Dimethyl Di(Hydrogenated Tallow) Ammonium Chloride

4 Commercially available as Polysurf D-67 from Aqualon.

Example 9

Shampoo Composition

Prepare a shampoo composition from the following components utilizing conventional mixing techniques.

| Ingredients | Weight % |
| --- | --- |
| Styling Agent | |
| Copolymer Premix from Example 7 | 15.00 |
| Silicone Premix | |
| Silicone gum | 0.50 |
| Dimethicone, 350 cs fluid | 0.50 |
| Main Mix | |
| Water | QS 100 |
| Ammonium lauryl sulfate | 11.00 |
| Cocamide MEA | 2.00 |
| Ethylene glycol distearate | 1.00 |
| Xanthan Gum | 1.20 |

| Ingredients | Weight % |
|---|---|
| Methylchloroisothiazolinone (and) methylisothiazolinone | 0.04 |

Citric Acid to pH 4.5 as needed

Prepare the Main Mix by first dissolving the xanthan gum in the water with conventional mixing. Add the remaining Main Mix ingredients and heat the mixture to 150° F. with agitation for ½ hour. Add the Styling Agent and the Silicone Premix sequentially with about 10 minutes of agitation between additions; stir the entire mixture while the batch is cooled to room temperature. For varied particle size, the Styling Agent and Silicone Premix are added at different times using either or both high shear mixing (high speed dispersator) or normal agitation.

Use the shampoo for cleansing the hair and for providing a styling benefit.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A hair care composition comprising:
   (A) a graft copolymer having a polymeric backbone and a hydrophobic polymeric side chain grafted to said backbone, said copolymer formed from the copolymerization of randomly repeating A monomer units and at least one B macromonomer unit wherein said copolymer comprises:
      (i) from about 30% to about 95% by weight of said A monomer units, wherein said A monomer units are monomer units copolymerizable with said B macromonomer units; and
      (ii) from about 5% to about 70% by weight of said B macromonomer units, wherein said B macromonomer units are hydrophobic macromonomer units having a polymeric portion and a moiety copolymerizable with said A monomer units; and
   wherein said A monomer units, in conjunction with said copolymerizable moieties of said B macromonomer units, form said backbone, the $T_g$ corresponding to said backbone having a value of at least about 25° C.;
   wherein said polymeric portion of said B macromonomer unit forms said hydrophobic side chain, the $T_g$ corresponding to said side chain having a value of less than about 10° C.; wherein said copolymer has a weight average molecular weight greater than about 10,000; and
   (B) a hydrophobic, volatile solvent for said copolymer, said solvent selected from the group consisting of branched hydrocarbons, silicones and combinations thereof.

2. A composition according to claim 1 wherein said A monomer units are ethylenically unsaturated monomer units, and said B macromonomer units are units having a polymeric portion and an ethylenically unsaturated moiety that is copolymerizable with said A monomer units.

3. A composition according to claim 2 wherein said A monomer units comprise hydrophobic monomers selected from the group consisting of: acrylic acid esters; methacrylic acid esters; N-alkyl acrylamides; vinyl compounds, vinylidene compounds; unsaturated hydrocarbons; $C_1$–$C_{18}$ alcohol esters of organic acids and organic acid anhydrides; and combinations thereof.

4. A composition according to claim 3 wherein said A monomer units comprise hydrophobic monomers selected from the group consisting of: acrylic or methacrylic acid esters of $C_1$–$C_{18}$ alcohols, dicyclopentenyl acrylate, 4-biphenyl acrylate, pentachlorophenyl acrylate, 3,5-dimethyladamentyl acrylate, 3,5-dimethyladamentyl methacrylate, 4-methoxycarbonylphenyl methacrylate, trimethylsilyl methacrylate, styrene, alpha-methylstyrene, t-butylstyrene, vinyl acetate, vinyl neononanoate, vinyl pivalate, vinyl propionate, vinyl chloride, vinylidene chloride, vinyl toluene, isobutyl vinyl ether, s-butyl vinyl ether, butadiene, cyclohexadiene, bicycloheptadiene, 2,3-dicarboxylmethyl-1,6-hexadiene, ethylene, propylene, indene, norbornylene, β-pinene, α-pinene, and combinations thereof.

5. A composition according to claim 4 wherein said A monomer units comprise hydrophobic monomers selected from the group consisting of n-butyl methacrylate, isobutyl methacrylate, t-butyl acrylate, t-butyl methacrylate, 2-ethylhexyl methacrylate, methyl methacrylate, indene, norbornylene, β-pinene, α-pinene, vinyl pivalate, vinyl neononanoate, dicyclopentenyl acrylate, 4-biphenyl acrylate, pentachlorophenyl acrylate, 3,5-dimethyladamantyl acrylate, 3,5-dimethyladamentyl methacrylate, 4-methoxycarbonylphenyl methacrylate, trimethylsilyl methacrylate, t-butyl styrene and combinations thereof.

6. A composition according to claim 5 wherein said A monomer units comprise hydrophobic monomers selected from the group consisting of t-butyl styrene, t-butyl acrylate, t-butyl methacrylate, and combinations thereof.

7. A composition according to claim 4 wherein said A monomer units further comprise hydrophilic monomers selected from the group consisting of unsaturated organic mono-and poly-carboxylic acids, (meth)acrylamides, (meth)acrylates, (meth)acrylate alcohols, organic acid anhydrides, esters of organic acid anhydrides, hydrophilic vinyl compounds, hydrophilic allyl compounds, hydrophilic imides, salts of the foregoing compounds, and combinations thereof.

8. A composition according to claim 2 wherein said B macromonomer units are of the formula (I) or (II):

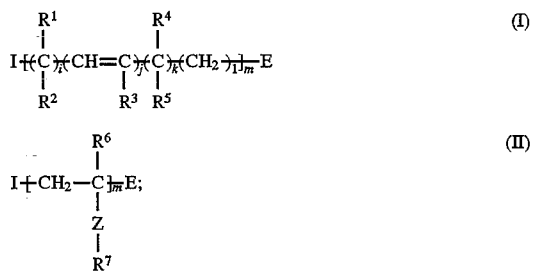

wherein $R^1$, $R^2$, $R^3$, $R^4$ and $R^5$ are, independently, H or $C_1$ to $C_5$ straight or branched alkyl group;

$R^6$=H or $C_1$ to $C_8$ alkyl $R^7$=$C_4$ to $C_{18}$

Z=

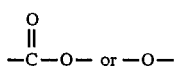

i and k are, independently, an integer of about 1 or greater;
j and l are, independently, an integer of about 0 or greater;
m is an integer from 10 about 2000;
E is an ethylenically unsaturated endcapping group copolymerizable with said A monomer units, selected from the group consisting of acrylamide, methacrylamide, vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, isoprenyl, cyclohexenyl, cyclopentenyl, and combinations thereof; and
I is a chemical initiator moiety.

9. The composition of claim 8 wherein E is selected from the group consisting of vinyl, alyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and combinations thereof.

10. The composition according to claim 9 wherein E is selected from the group consisting of vinyl, allyl, acryloyl, methacryloyl, ethacryloyl, 3-vinylbenzyl, 4-vinylbenzyl, and combinations thereof.

11. The composition according to claim 10 wherein said B macromonomer units are selected from the group consisting of acryloyl, methacryloyl, or 2-,3- or 4-vinyl benzyl endcapped polymers of: methacrylic or acrylic acid esters, poly(alkenes), hydrogenated poly(alkenes), poly(vinyl ethers), poly(vinyl benzenes), and combinations thereof.

12. The composition according to claim 8 wherein said B macromonomer units are selected from the group consisting of acryloyl, methacryloyl, or 2-,3- or 4-vinyl benzyl endcapped polymers of: poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(isodecyl acrylate), poly(iso-propyl acrylate), poly(3-methylbutyl acrylate), poly(2-methylpentyl acrylate), poly (nonyl acrylate), poly(octyl acrylate), poly(propyl acrylate), poly (2-ethylhexyl methacrylate), poly(tridecyl methacrylate), poly(hexyl methacrylate), poly(decyl methacrylate), poly(octyl methacrylate), poly(octadecyl methacrylate), poly(dodecyl methacrylate), poly(n-pentyl methacrylate), poly(isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly (6-methyl-1-heptene), poly(4,4-dimethyl-1-pentene), poly (iso-butyl vinyl ether), poly[4-t-butyl vinyl benzene-co-2-ethylhexyl acrylate], poly[2-ethylhexyl acrylate-co-octyl acrylamide), poly[2-ethyl vinyl benzene-co-octyl methacrylate)], and combinations thereof.

13. A composition according to claim 1 wherein said graft copolymer is selected from the group consisting of Poly [poly(tert-butylacrylate)-graft-poly(isobutylene) macromonomer], Poly[poly(4-tert-butylstyrene)-graft-poly (isobutylene) macromonomer], Poly[(4-tert-butylstyrene)-graft-poly(2-ethylhexyl methacrylate) macromonomer], Poly[(tert-butylacrylate-co-styrene)-graft-poly (isobutylene)], and combinations thereof.

14. A composition according to claim 1 wherein said solvent is selected from the group consisting of branched chain hydrocarbons containing from 10 to 16 carbon atoms and combinations thereof.

15. A composition according to claim 14 wherein said solvent is selected from the group consisting of branched chain hydrocarbons containing from 12 to 16 carbon atoms and combinations thereof.

16. A composition according to claim 15 wherein said solvent comprises isododecane.

17. A composition according to claim 1 wherein said solvent is a silicone.

18. A composition according to claim 1 comprising from about 0.1% to about 25% of said copolymer and from about 0.1% to about 75% of said solvent.

19. A composition according to claim 1 wherein the copolymer exhibits at least two distinct $T_g$ values, one of said $T_g$s corresponding to said hydrophobic polymeric side chains and having a value of less than about 10° C., another of said $T_g$s corresponding to said backbone and having a value of at least about 25° C.

20. The composition of claim 1 further comprising an aqueous carrier for said graft copolymer and said solvent.

21. A method for styling hair comprising applying the composition of claim 1 to the hair in an amount sufficient to style the hair.

22. A method for conditioning hair comprising applying the composition of claim 1 to the hair in an amount sufficient to condition the hair.

* * * * *

UNITED STATES PATENT AND TRADEMARK OFFICE
CERTIFICATE OF CORRECTION

PATENT NO. : 5,632,998
DATED : May 27, 1997
INVENTOR(S) : Sanjeev Midha and Raymond E. Bolich, Jr.

It is certified that error appears in the above-indentified patent and that said Letters Patent is hereby corrected as shown below:

At column 3, lines 33-37 "  " should read --  --.

At column 3, line 55 "4-vinylbenzoyl-1-butenyl" should read --4-vinylbenzyl, 1-butenyl--.

At column 5, line 11 "lover" should read --lower--.

At column 7, line 46 "B Macromonomers" should read --B macromonomers--.

At column 8, lines 41-42 "3,5-dimethyladamentyl" should read --3,5-dimethyladamantyl--.

At column 8, line 43 "4-methoxycarbonyphenyl" should read --4-methoxycarbonylphenyl--.

At column 10, lines 36-40 "  " should read --  --.

At column 11, line 8 "carbanions" should read --carbocations--.

At column 11, line 18 "1,1-diphenyl14-methylpentyl" should read --1,1-diphenyl-4-methylpentyl--.

At column 11, line 30 "selectcd" should read --selected--.

At column 11, line 66 "polymerzing" should read --polymerizing--.

At column 12, line 38 "avenge" should read --average--.

At column 12, line 42 "avenge" should read --average--.

At column 12, line 43 "avenge" should read --average--.

At column 13, line 60 "point or the" should read --point of the--.

UNITED STATES PATENT AND TRADEMARK OFFICE
CERTIFICATE OF CORRECTION

PATENT NO.    :    5,632,998

DATED         :    May 27, 1997

INVENTOR(S)   :    Sanjeev Midha and Raymond E. Bolich, Jr.

It is certified that error appears in the above-identified patent and that said Letters Patent is hereby corrected as shown below:

At column 14, line 24 "Isopar™ and K" should read --Isopar™ H and K--.

At column 14, lines 24-25 "Isopar™ ($C_{11}$-$C_{13}$ isoparaffins)" should read --Isopar™ L ($C_{11}$-$C_{13}$ isoparaffins)--.

At column 14, line 26 "lsododecane" should read --Isododecane--.

At column 14, line 32 "methox3propyl" should read --methoxypropyl--.

At column 14, line 65 "theology" should read --rheology--.

At column 15, line 2 "theology" should read --rheology--.

At column 15, line 36 "D. Swem" should read --D. Swern--.

At column 15, line 40 "Villamarin, et at.," should read --Villamarin, et al.,--.

At column 15, line 43 "*Toiletties*" should read --*Toiletries*--.

At column 15, line 59 "glueart" should read --glucan--.

At column 16, line 31 "Pansher-Jackson et at." should read --Ansher-Jackson et al.--.

At column 18, line 14 "oilrate" should read --citrate--.

At column 20, line 1 "Laughlin et at." should read --Laughlin et al.--.

At column 20, line 35 "bend" should read --bond--.

At column 20, line 43 "about i0" should read --about 10--.

At column 20, line 60 "surfoxide" should read --sulfoxide--.

At column 20, line 61 "surfoxide" should read --sulfoxide--.

At column 21, line 43 "chlorides" should read --chloride--.

At column 22, line 28 "phosphors" should read --phosphorus--.

At column 23, line 14 "Dow Coming" should read --Dow Corning--.

UNITED STATES PATENT AND TRADEMARK OFFICE
CERTIFICATE OF CORRECTION

PATENT NO. : 5,632,998
DATED : May 27, 1997
INVENTOR(S) : Sanjeev Midha and Raymond E. Bolich, Jr.

Page 3 of 4

It is certified that error appears in the above-identified patent and that said Letters Patent is hereby corrected as shown below:

At column 23, line 23 "polyalkyl" should read --polyalkylaryl--.

At column 24, line 8 "556°" should read --556--.

At column 25, line 44 "convened" should read --converted--.

At column 25, line 50 "action" should read --anion--.

At column 25, line 55 "monoalkyl-aminoalkyl" should read --monoalkylaminoalkyl--.

At column 25, line 62 "salts, The" should read --salts. The--.

At column 26, line 54 "cationic. cellulose" should read --cationic cellulose--.

At column 28, line 34 "cathoxylic" should read --carboxylic--.

At column 29, line 58 "0.048 m" should read --0.048 mol--.

At column 29, line 65 "macremonomer" should read --macromonomer--.

At column 30, line 11 "macremoners" should read --macromonomers--.

At column 30, line 18 "graft-poly" should read --graft-[poly--.

At column 30, line 22 "graft-poly" should read --graft-[poly--.

At column 30, line 25 "macremonomer" should read --macromonomer--.

At column 32, line 17 "Hydroxythyl" should read --Hydroxyethyl--.

At column 32, line 25 "mixure" should read --mixture--.

At column 34, line 10 the first occurrence of "dimethyladamentyl" should read --dimethyladamantyl--.

At column 35, lines 1-5 "$Z=\overset{O}{\overset{\|}{-C}}-O-$ or $-O-$" should read --$Z=\overset{O}{\overset{\|}{-C}}-O-$ or $-O-$--.

UNITED STATES PATENT AND TRADEMARK OFFICE
CERTIFICATE OF CORRECTION

PATENT NO.      :   5,632,998

DATED           :   May 27, 1997

INVENTOR(S)     :   Sanjeev Midha and Raymond E. Bolich, Jr.

It is certified that error appears in the above-identified patent and that said Letters Patent is hereby corrected as shown below:

At column 35, line 13 "ethacnyloyl" should read --ethacryloyl--.

At column 35, line 15 "vinylbcnzoyl" should read --vinylbenzoyl--.

At column 35, line 21 "alyl" should read --allyl--.

At column 35, line 22 "vinylbcnzoyl" should read --vinylbenzoyl--.

At Col. 19, line 64, "Many" begins a new paragraph.

Signed and Sealed this

Eleventh Day of November, 1997

Attest:

BRUCE LEHMAN

Attesting Officer

Commissioner of Patents and Trademarks